(12) United States Patent
Young et al.

(10) Patent No.: US 8,287,452 B2
(45) Date of Patent: Oct. 16, 2012

(54) APPARATUS FOR MONITORING VITAL SIGNS OF AN EMERGENCY VICTIM

(75) Inventors: Steven J. Young, Los Gatos, CA (US); Richard V. Rifredi, Los Gatos, CA (US); Yuri Zhovnirovsky, Albany, CA (US)

(73) Assignee: BAM Labs, Inc., Campbell, CA (US)

( * ) Notice: Subject to any disclaimer, the term of this patent is extended or adjusted under 35 U.S.C. 154(b) by 826 days.

(21) Appl. No.: 12/349,853

(22) Filed: Jan. 7, 2009

(65) Prior Publication Data
US 2010/0174199 A1  Jul. 8, 2010

(51) Int. Cl.
*A61B 5/08* (2006.01)
*A61B 5/103* (2006.01)

(52) U.S. Cl. ........ 600/301; 600/595; 340/592; 340/665; 340/666; 340/686.1

(58) Field of Classification Search .......... 340/575, 340/665, 666, 667, 686.1, 693.5, 592; 200/85; 177/144; 73/172; 600/301, 595
See application file for complete search history.

(56) References Cited

U.S. PATENT DOCUMENTS

| | | | |
|---|---|---|---|
| 5,469,592 A * | 11/1995 | Johnson | 5/654 |
| 6,848,135 B1 | 2/2005 | Kohlman | |
| 7,330,127 B2 * | 2/2008 | Price et al. | 340/666 |
| 2005/0022606 A1 * | 2/2005 | Partin et al. | 73/773 |
| 2005/0154336 A1 | 7/2005 | Kloecker et al. | |
| 2005/0190068 A1 * | 9/2005 | Gentry et al. | 340/665 |
| 2008/0060138 A1 | 3/2008 | Price et al. | |
| 2008/0077020 A1 | 3/2008 | Young et al. | |

FOREIGN PATENT DOCUMENTS

| | | |
|---|---|---|
| JP | 2004-049838 A | 2/2004 |
| JP | 2004-113618 A | 4/2004 |
| JP | 2004-130012 A | 4/2004 |
| JP | 2007-125337 A | 5/2007 |
| JP | 2008-259745 A | 10/2008 |
| JP | 2010-094379 A | 4/2010 |

OTHER PUBLICATIONS

Notification of Transmittal, International Search Report and Written Opinion of the International Searching Authority (ISA/KR) dated Aug. 13, 2010 from the corresponding International Patent Application No. PCT/US2010/020205.

* cited by examiner

*Primary Examiner* — Gail R Gabel
(74) *Attorney, Agent, or Firm* — Young Basile

(57) ABSTRACT

A portable apparatus for monitoring on site near an emergency field at least one vital sign of a patient reclined thereon includes a fluid bladder transformable between a stowable arrangement and a deployed arrangement. The fluid bladder in the deployed arrangement has a comfortable top surface of sufficient size to fully support at least a torso of the patient in a reclined position, and the fluid bladder has a ruggedized puncture resistant bottom layer. A sensor is configured to detect a pressure within the fluid bladder. A controller is configured to determine the at least one vital sign based on the pressure within the fluid bladder. A triage condition indicator is configured to indicate a care urgency level based on the at least one vital sign.

20 Claims, 2 Drawing Sheets

APPARATUS FOR MONITORING VITAL SIGNS OF AN EMERGENCY VICTIM

FIELD OF THE INVENTION

The present invention pertains to a vital sign monitoring apparatus.

BACKGROUND

Historically, monitoring vital signs of a person has required expensive equipment, such as an electrocardiogram (EKG) or a ballistocardiograph (BCG). In addition to being prohibitively expensive for many situations (e.g., ownership by a police or fire department of more than a few devices), both EKGs and BCGs can be too cumbersome for use outside of medical facilities. EKGs, for example, typically necessitate attaching electrodes to the bodies of users, while BCGs rely on large, heavy, and unaesthetic force-measuring platforms that users lie on.

In more recent times, devices including piezoelectric films or arrays of sensors have been developed to measure heart and respiration rates. A user can lie on the device, and the film or sensors can generate a signal indicate of the user's heart rate and/or respiration rate. However, these devices can also be expensive.

SUMMARY

In one example, a portable apparatus for monitoring on site near an emergency field at least one vital sign of a patient reclined thereon is provided. The apparatus includes a fluid bladder transformable between a stowable arrangement and a deployed arrangement. The fluid bladder in the deployed arrangement has a comfortable top surface of sufficient size to fully support at least a torso of the patient in a reclined position, and the fluid bladder has a ruggedized puncture resistant bottom layer. A sensor is configured to detect a pressure within the fluid bladder. A controller is configured to determine the at least one vital sign based on the pressure within the fluid bladder. A triage condition indicator is configured to indicate a care urgency level based on the at least one vital sign.

In another example, an apparatus for monitoring vital signs of multiple persons is provided. The apparatus includes multiple patient beds. Each patient bed includes a fluid bladder and a sensor configured to detect a pressure within the fluid bladder. A controller is configured to determine the vital signs based on the pressures within the fluid bladders. A triage condition indicator is configured to indicate a care urgency level for at least one of the multiple patient beds based on the at least one vital sign.

BRIEF DESCRIPTION OF THE DRAWINGS

The description herein makes reference to the accompanying drawings, wherein like reference numerals refer to like parts throughout the several views, and wherein.

DETAILED DESCRIPTION

Figure 1:
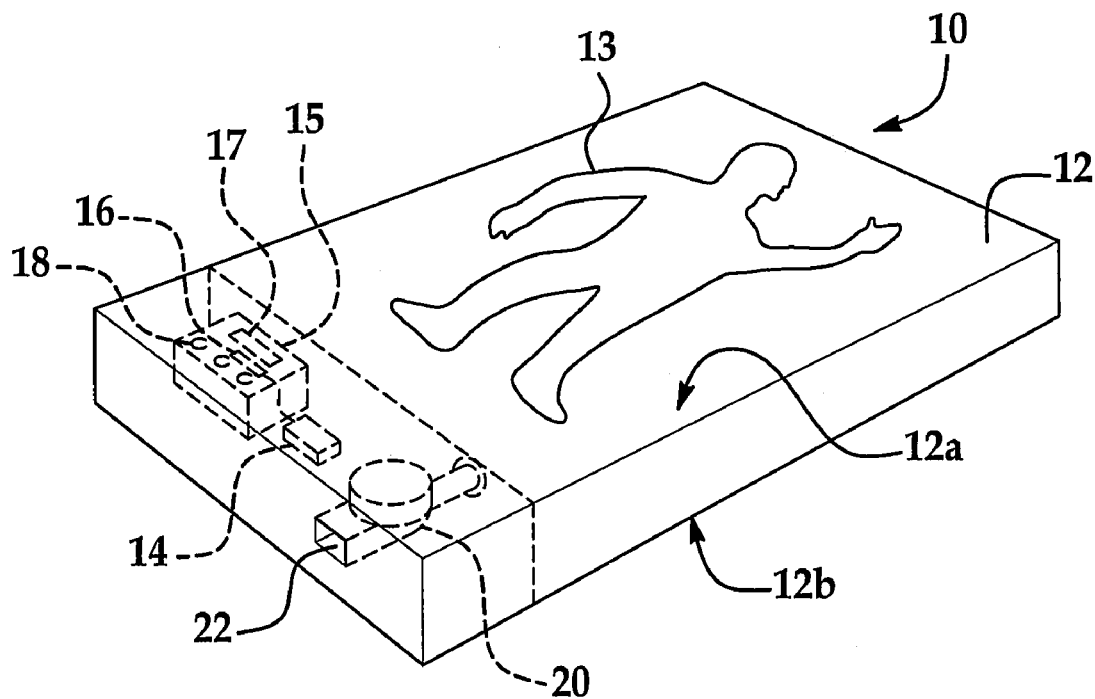
FIG. 1 is a perspective view of an example of an emergency victim monitoring system in a deployed arrangement for use by an individual patient.

As shown in FIG. 1, an apparatus 10 for monitoring at least one vital sign of a patient 13 lying thereon can include a fluid bladder 12, a sensor 14, a control unit 15, and a pump 20. The apparatus 10 can measure a heart rate, a respiratory rate, and/or other vital signs of the patient 13 lying on the fluid bladder 12 as is explained below.

The fluid bladder 12 can contain air or another fluid (e.g., water). The bladder 12 can define a single fluid compartment. Alternatively, the bladder 12 can define multiple compartments, in which case each compartment from which a pressure measurement is desired can include a sensor 14. The bladder 12 can be in fluid communication with the pump 20, such that the pump 20 can inflate the bladder 12.

The bladder 12 can be sized to comfortably accommodate a patient 13 of ordinary size (e.g., the bladder 12 can be seven feet long by four feet wide such that even large patients 13 can be accommodated). However, the bladder 12 can have a different structure from as shown in FIG. 1. For example, the bladder 12 can have a smaller size, such as a size sufficient to fully support only a torso area of a patient 13 (e.g., the bladder 12 can be two feet long by three feet wide to accommodate an ordinarily sized torso even if the patient 13 is not centered on the bladder 12), and the smaller-sized bladder 12 can be integral with another type of pad for supporting the remainder of the patient 13. As another example, a foam pad including an air bladder near an area where the patient's heart and/or lungs are expected to be positioned can be used instead of the illustrated bladder 12.

Additionally, the bladder 12 can include a comfortable (e.g., soft and/or flexible) top surface 12a. The top surface 12a can include a layer of foam or some other type of padding, such as a thin fluid or gel filled layer. Alternatively, the pressure of the fluid 12a within the fluid bladder 12 can be sufficient to make the top surface 12a comfortable. The top surface 12a can also include a hydrophobic material for easy cleaning. For example, the use of a hydrophobic material can allow fluid to be easily wiped off the top surface 12a. The hydrophobic material can be a coating such as Duralon UltraTec by Cotec-GmbH or another hydrophobic material. Additionally, the top surface 12a can be covered with a disposable protective covering, and a new covering can be provided for each patient 13 for health and safety reasons.

The bladder 12 can include a ruggedized puncture resistant layer 12b on its bottom to reduce the likelihood of puncture if, for example, the bladder 12 is placed on the ground in an area with sharp debris such as glass or metal shards, a nail or screw, or a similar object. The ruggedized puncture resistant layer 12b can be a layer of material of sufficient thickness to prevent the bladder 12 from being punctured if the bladder 12 encounters sharp debris such as glass or metal shards, a nail or screw, or a similar object. For example, the layer 12b can be 0.01" thick to 0.25" thick, though the layer 12b can have an alternative thickness depending on its material. The layer 12b can be made from a high strength material such as Kevlar, though other materials (e.g., rubber) can additionally or alternatively be used. Puncture resistance can also be provided by including a sealant within the fluid bladder 12.

The pressure within the fluid bladder 12 should be sufficient to suspend the patient 13 without the patient 13 contacting the ground or other surface beneath the bladder 12. However, even when a constant amount of fluid is in the bladder 12, the pressure in the fluid bladder 12 can vary depending on the temperature of the fluid in the bladder 12, whether the patient 13 is lying on the bladder 12 and, when the patient 13 is lying on the bladder 12, the heart rate of the patient 13, the respiration rate of the patient 13, other movement of the patient 13 (e.g., rolling or limb movement), and other considerations.

The sensor 14 can include a semiconductor pressure sensor or another type of pressure sensor. The sensor 14 can be positioned to detect the pressure in the fluid bladder 12. For example, the sensor 14 can be inside the fluid bladder 12 as shown in FIG. 1. As a result, a pressure signal output by the sensor 14 can correspond to the heart rate of the patient 13 lying on the bladder 12, the respiration rate of the patient 13 lying on the bladder 12, movement of the patient 13 lying on the bladder 12, and other considerations. The sensor 14 can be in communication with the control unit 15 by hard-wiring the sensor 14 and control unit 15, by wireless communication (e.g., using, a standard wireless protocol such as IEEE 802.11, 3G, or Bluethooth), or using another connection, enabling the sensor 14 to communicate the pressure signal corresponding to the pressure in the bladder 12 to the control unit 15. Also, the apparatus 10 can include additional, sensors, such as more than one sensor 14, a dedicated temperature sensor, and other types of sensors.

The control unit 15 can include a controller 16, a display screen 17, and controls 18. The control unit 15 can be integral with the fluid bladder 12 as shown in FIG. 1. For example, a body of the control unit 15 including the controller 16 can be below the top surface 12a of the bladder 12, while the display screen 17 can be visible and the controls 18 can be accessible near the top surface 12a of the bladder 12. Alternatively, the control unit 15 can have a different configuration from as shown. For example, the control unit 15 can be a separate unit from the bladder 12 and in communication with the sensor 14.

The controller 16 can include a memory and a CPU for executing a program stored on the memory. The controller 16 can be in communication with the pump 20 (e.g., by hard-wiring the controller 16 to the pump 20 or by wireless communication therebetween) to control the operation of the pump 20. For example, the controller 16 can control the pump 20 to inflate the bladder 12 when the sensor 14 indicates the pressure in the bladder 16 is below a set amount (e.g., an amount entered via the controls 18).

Additionally, the controller 16 can analyze the pressure signal output by the sensor to determine a heart rate, respiration rate, and/or other vital signs of the patient 13 lying or sitting on the fluid bladder 12. Since the pressure signal can include a change in pressure for each heart beat, breath, or other movement of the patient 13 on the bladder 12, the controller 16 can use an algorithm or other calculation to determine the heart rate and respiratory rate of the patient 13. For example, the algorithm or calculation can be based on assumptions that a heart rate portion of the signal $\alpha$ has a frequency in the range of 0.5-4.0 Hz and that a respiration rate portion of the signal a has a frequency in the range of the range of less than 1 Hz. The pressure signal can be filtered and/or amplified prior to being analyzed by the controller 16. The controller 16 can also be configured to determine other vital indications of the patient 13 based on the pressure signal, such as whether the patient 13 is present, the blood pressure of the patient 13, tossing and turning movements, rolling movements, limb movements, weight, and the identity of the patient 13. Further, the controller 16 can receive signals from other sensors (e.g., a temperature sensor). The controller 16 can output a status signal indicating the characteristics of the patient 13 (e.g., heart rate and respiratory rate) to the display 17. Additionally, the apparatus 10 can include a transmitter for wirelessly or otherwise transmitting the patient's vital signs and/or other information to a remote location, such as a triage.

In addition, the controller 16 can calculate a care urgency level based on the heart rate, respiration rate, weight, blood pressure, presence, weight, amount of movement and/or other considerations determined based on the pressure detected by the sensor 14 or otherwise input to the apparatus 10. For example, the care urgency level can indicate the urgency with which care should be given to the patient 13, such as whether the patient 13 needs immediate attention, and the care urgency level can be used either alone or in conjunction with a care urgency value of another apparatus 10 to determine an order of care. The care urgency level can be a multi-level indication (e.g., low, medium, and high) or an urgency ranking (e.g., most urgent, second most urgent, etc.).

The display 17 can display vital signs, such as heart rate, respiratory rate, frequency and/or amount of movement, and other information. In addition, the display 17 can display the care urgency level. As a result, the display 17 in conjunction with the controller 16 can form a triage condition indicator for indicating the care urgency level. However, another device such as a speaker, a transmitter in communication wirelessly or otherwise with a notification device (e.g., a pager, a triage station or a cell-phone), a flag or some other notification device can additionally or alternatively act as a triage condition indicator by indicating the care urgency level. The display 17 can produce an alarm based on vitals signs and/or the triage value, for example by flashing or changing colors when the triage value suggests a high care urgency level.

The controls 18 can be used to control the operation of the sensor 14 and/or controller 16. For example, the controls 18 can be used to increase the air pressure in the bladder 12, to enter age or weight information regarding the patient 13, to enter the patients's health history (e.g., allergies or prescriptions currently being taken), and to perform other controls.

The pump 20 can be a rotary type pump or another type of pump. An inlet portion of pump 20 can be fluidly coupled to the ambient environment via a vent 22, and an outlet portion of the pump can be fluidly coupled to the bladder 12 for inflating the bladder 20. The pump 20 can be integral with the bladder 12, though the pump 20 can alternatively be a separate unit coupled to the bladder 12 via a hose. Additionally, a single pump 20 can be coupled to multiple bladders 22. The pump 20 can be in communication with the control unit 15, allowing the at least one of the controller 16 and the controls 18 to control operation of the pump 20. The control unit 15 and pump 20 can be package in a hard-shell portion of the apparatus 10 to provide protection.

Figure 2:
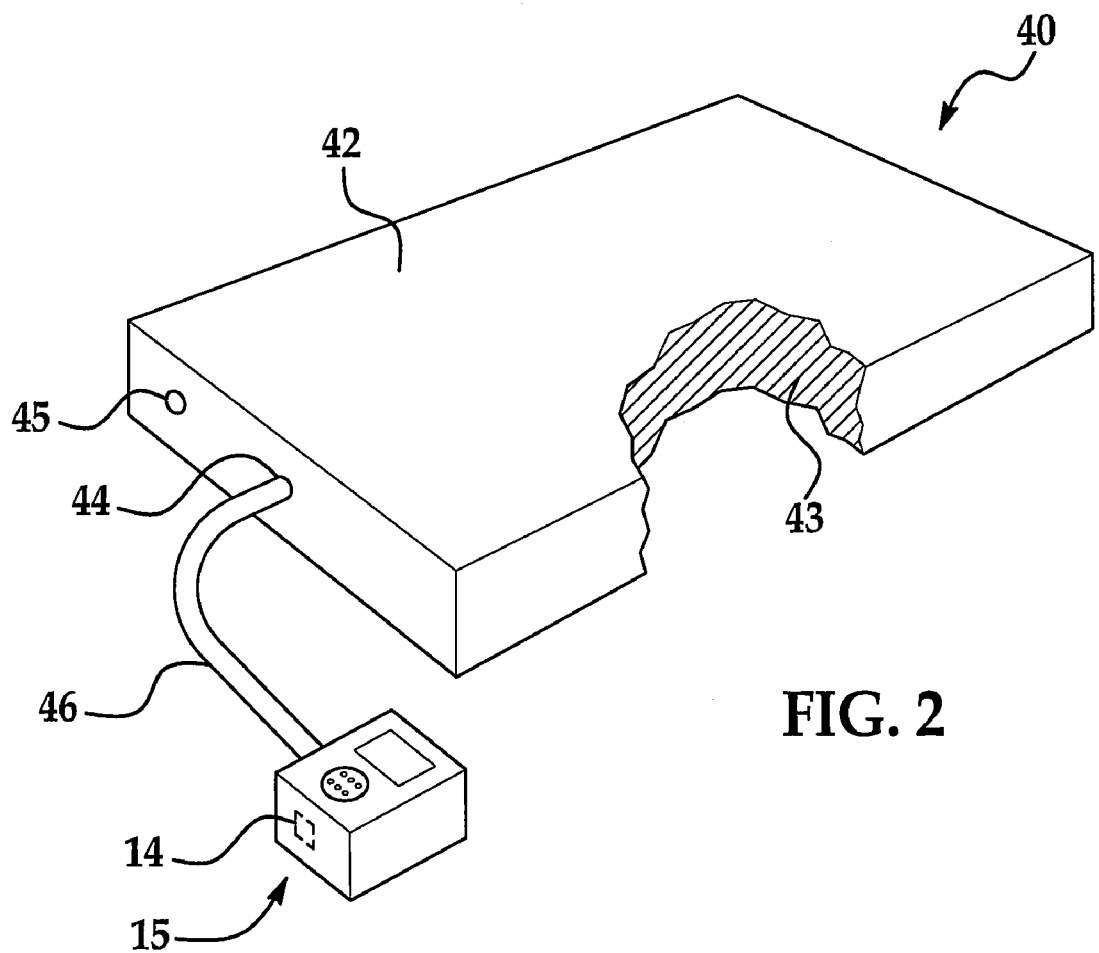
FIG. 2 is a perspective view of another example of an emergency victim monitoring system in a deployed arrangement.

Another example of an apparatus 40 for monitoring at least one vital sign of a patient lying thereon can include a self-inflating fluid bladder 42 fluidly coupled to the control unit 15. The fluid bladder 42 can contain foam 43 or another material that urges the bladder 42 to expand to a deployed position, which is the position of the bladder 42 as shown in FIG. 2, and that allows fluid waves to propagate through the bladder 42. The fluid bladder 42 can include a fluid inlet, such as the illustrated one-way valve 45, for allowing fluid into the fluid bladder 42. In operation, when deployed from a deflated state, the foam 43 can urge the fluid bladder 42 to expand, creating a vacuum that draws fluid through the valve 45. The use of the one-way valve 45 can prevent fluid from being forced out of the bladder 42 when a patient rests thereon. The fluid bladder 42 can additionally include a fluid outlet 44 for releasing fluid from the bladder 42 to return the bladder 42 to a stowed position. In this example, the control unit 15 includes the sensor 14, and a hose 46 is attached to the fluid outlet 44 of the fluid bladder 42 and to the control unit 15, thereby fluidly coupling the sensor 14 to the fluid bladder 42. As a result, pressure fluctuations in the fluid bladder 42 can be detected by the sensor 14, and the sensor 14 can relay the detected pressure to a controller (e.g., a microprocessor) or a similar device in the control unit 15 for determining a vital sign, such as a heart-rate and/or respiration rate, of a patient on the bladder 42. The self-inflating fluid bladder 42 can have a different configuration from as shown, such as by including the bladder 42 and sensor 14 in a single package along with a transmitter to relay the pressure detected by the sensor 14 to a remote controller for determining vital signs.

Figure 3:
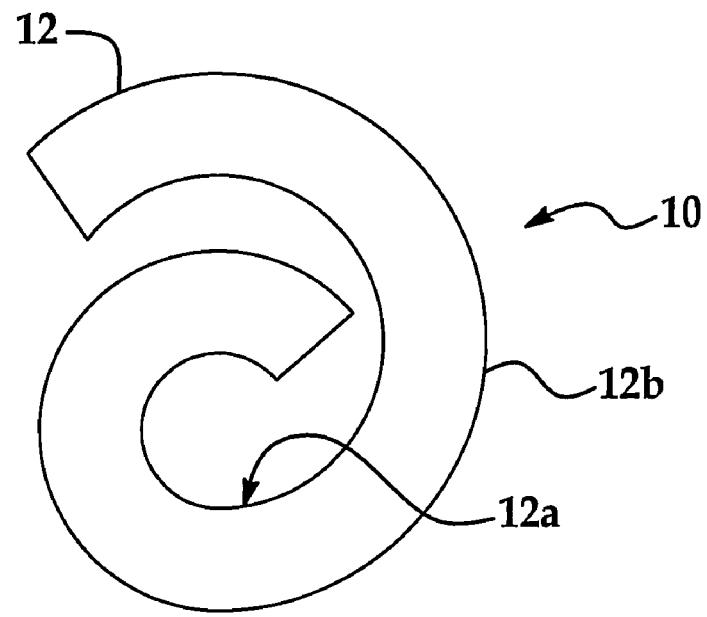
FIG. 3 is a schematic view of the emergency victim monitoring system of FIG. 1 in a stowable arrangement.

While the apparatuses 10 and 40 are shown in FIGS. 1 and 2, respectfully, in deployed arrangements in which the patient 13 can recline thereon, the apparatuses 10 and 40 can also be arranged in a stowable arrangement. For example, the bladder 12 can be transformed into a stowable arrangement as shown in FIG. 3 by deflating the bladder 12 then wrapping up or otherwise rearranging the bladder 12. Alternatively, the bladder 12 can be arranged to be stowed by folding the bladder 12 or otherwise reducing the footprint of the bladder 12.

To transform the bladder 12 from the stowable arrangement to the deployed arrangement, any straps or other connectors holding the bladder 12 in the stowable arrangement can be undone and the bladder 12 can be inflated using the pump 20. Alternatively, the apparatus 10 can include a fluid source other than the pump 20. For example, the apparatus 10 can include a source of compressed fluid (e.g., a $CO_2$ cartridge) that can be actuated to rapidly fill the bladder 12. As another example, the self-inflating bladder 42 described above can automatically intake fluid.

Since the bladder 12, sensor 14, control unit 15, and pump 20 can be part of an integrally packaged unit that is stowable, the apparatus 10 can be more easily transported and deployed than a monitor include separate parts or parts that are not stowable. Further, the apparatus 10 can provide the urgency care level to make it easier to determine a proper order of care. Also, the urgency care level can provide an alert when care is needed very urgently. Additionally, the construction of the apparatus 10 (e.g., having a comfortable top layer 12a and ruggedized puncture resistant bottom layer 12b) can make the apparatus 10 suitable for use in an emergency field where debris may be present.

Figure 4:
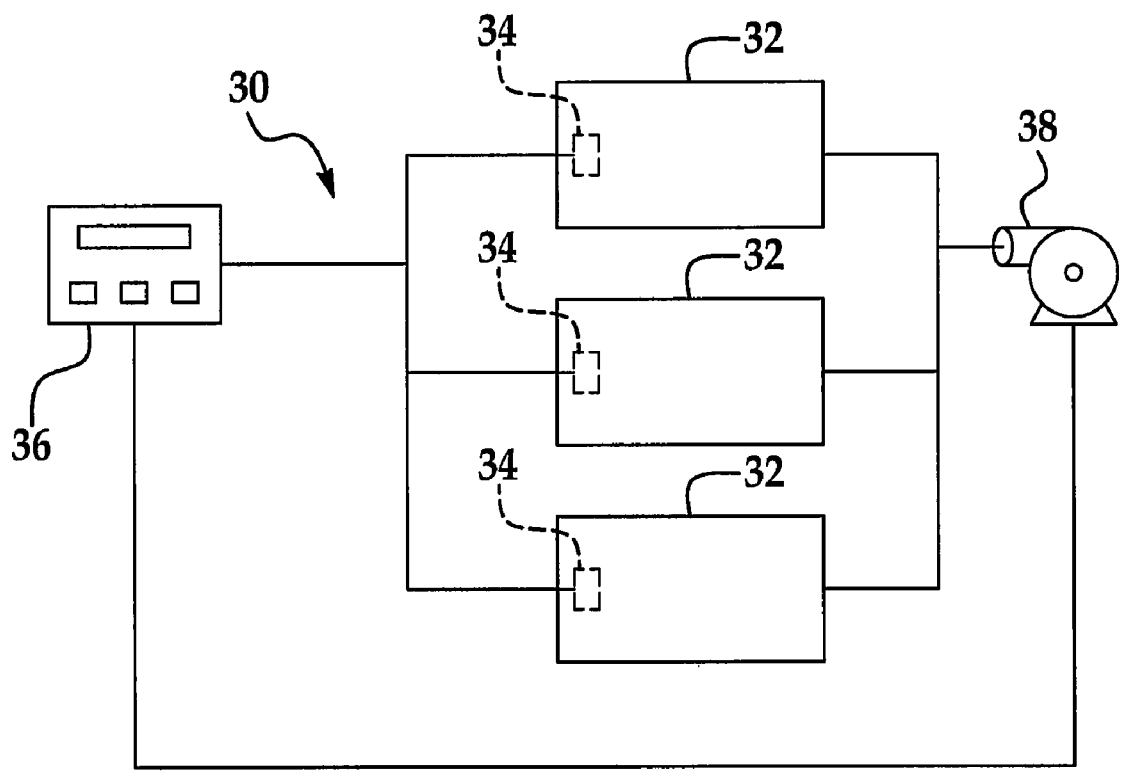
FIG. 4 is a schematic view of an example of another emergency victim monitoring system for use by a group of people.

Another example of an apparatus 30 for monitoring vital signs of multiple patients lying thereon including multiple air bladders 32, each including a sensor 34, is shown in FIG. 4. The bladders 32 and sensors 34 can be similar to the bladder 12 and sensor 14 described above with respect of FIG. 1, or to the bladder 42 and sensor 14 described above with respect to FIG. 2. For example, the sensors 34 can measure the pressures in the respective bladders 32. The sensors 34 can be in communication with a control unit 36. The control unit 36 can include controls, a display, and a controller for determining vital signs (e.g., heart rates and respiration rates) similar to the control unit 15 as described in respect to FIG. 1. However, a single control unit 36 can be used to determine the vital signs of multiple patients, as opposed to using dedicated control unit for each bladder 32. Further, the control unit 36 can include rank an urgency of care for the patients on the bladders 32. As a result, the control unit 36 can function as a triage station. Additionally, a single pump 38, similar to the pump 20 described with respect to FIG. 1, can be in fluid communication with multiple bladders 32. The pump 38 can additionally be in communication with the sensors 34 and/or the control unit 36.

While the invention has been described in connection with what is presently considered to be the most practical example, it is to be understood that the invention is not to be limited to the disclosed example but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed:

1. A portable apparatus for monitoring at least one vital sign of a subject in a medical emergency at an emergency site, the apparatus comprising:

a fluid bladder transformable between a stowable arrangement having a first footprint and a deployed arrangement having a second footprint, the second footprint being larger than the first footprint, the fluid bladder in the deployed arrangement having a top surface of sufficient size to fully support at least a torso portion of the subject in a reclined position and having a puncture resistant bottom layer configured for use at the emergency site, the fluid bladder having a sensor integral with the fluid bladder and in fluid communication with a fluid within the fluid bladder, the sensor configured to detect a pressure within the fluid bladder from the subject positioned on the fluid bladder;

a controller configured to determine the at least one vital sign of the subject positioned on the fluid bladder from changes in the pressure within the fluid bladder due to the subject positioned on the fluid bladder; and a triage condition indicator configured to indicate a care urgency level based on the at least one vital sign of the subject, wherein the fluid bladder comprises a fluid outlet configured to release fluid from the fluid bladder, and wherein the sensor is fluidly coupled to the fluid outlet and configured to detect pressure fluctuations within the fluid bladder via the fluid outlet.

2. The apparatus of claim 1, wherein the top surface of the fluid bladder is hydrophobic.

3. The apparatus of claim 1, further comprising a pump in fluid communication with the fluid bladder.

4. The apparatus of claim 3, wherein the pump and fluid bladder are integrally packaged.

5. The apparatus of claim 1, further comprising a display configured to show at least one of the vital sign and the triage value.

6. The apparatus of claim 5, wherein the display and fluid bladder are integrally packaged.

7. The apparatus of claim 1, wherein the vital sign includes at least one of heart rate, respiration rate, and movement of the subject positioned on the fluid bladder.

8. The apparatus of claim 1, wherein the controller is further configured to produce an alarm instruction when the at least one vital sign is outside of a predetermined acceptable range.

9. The apparatus of claim 1, wherein the fluid bladder is self-inflating.

10. The apparatus of claim 1, further comprising a plurality of fluid bladders each configured to support a respective subject and each having a respective sensor as defined in claim 1, each of the respective sensors communicating with the controller.

11. The apparatus of claim 10, wherein the controller is further configured to determine the care urgency level of each of the respective subjects and rank the care urgency levels, with the triage condition indicator further configured to indicate a ranking of care urgency levels.

12. The apparatus of claim 11, wherein the controller is preprogrammed with a plurality of degrees of care urgency levels and is configured to produce an alarm instruction when one or more of the care urgency levels in the ranking is above a threshold degree of care urgency levels.

13. The apparatus of claim 10, further comprising a display in communication with each of the plurality of fluid bladders and configured to show one or both of the at least one of the vital sign and the care urgency level for each of the respective subjects.

14. The apparatus of claim 10, wherein the vital signs include at least one of heart rate, respiration rate, and movement of the subject positioned on the fluid bladder.

15. The apparatus of claim 10, wherein the plurality of fluid bladders each have a puncture resistant bottom layer configured for outdoor use.

16. The apparatus of claim 10, wherein each of the plurality of fluid bladders includes its own distinct triage condition indicator.

17. The apparatus of claim 16, wherein the plurality of fluid bladders are self-inflating.

18. The apparatus of claim 1, wherein the controller is located within the fluid bladder and the triage condition indicator communicates with the controller wirelessly and is remotely located from the fluid bladder, sensor and controller.

19. The apparatus of claim 1, wherein the stowable arrangement comprises the fluid bladder empty of fluid and in a rolled configuration.

20. The apparatus of claim 1, wherein the controller is further configured to determine a presence of the subject on the fluid bladder from the pressure within the fluid bladder.

* * * * *